(12) United States Patent
Young et al.

(10) Patent No.: US 7,348,413 B2
(45) Date of Patent: Mar. 25, 2008

(54) CANCEROUS DISEASE MODIFYING ANTIBODIES

(75) Inventors: David S. F. Young, Toronto (CA); Susan E. Hahn, Toronto (CA); Lisa M. Cechetto, Ancaster (CA)

(73) Assignee: Arius Research Inc., Toronto, Ontario (CA)

( * ) Notice: Subject to any disclaimer, the term of this patent is extended or adjusted under 35 U.S.C. 154(b) by 154 days.

(21) Appl. No.: 11/067,390

(22) Filed: Feb. 25, 2005

(65) Prior Publication Data

US 2005/0191306 A1    Sep. 1, 2005

Related U.S. Application Data

(60) Provisional application No. 60/548,531, filed on Feb. 26, 2004.

(51) Int. Cl.
*C07K 16/00* (2006.01)
*C12P 21/08* (2006.01)
*A61K 39/00* (2006.01)
*G01N 33/53* (2006.01)
*A61K 39/395* (2006.01)

(52) U.S. Cl. .................... 530/387.1; 530/387.3; 530/388.1; 530/388.8; 530/391.1; 424/133.1; 424/141.1; 424/155.1; 424/174.1; 435/7.1

(58) Field of Classification Search .............. None
See application file for complete search history.

(56) References Cited

U.S. PATENT DOCUMENTS

| | | | |
|---|---|---|---|
| 4,433,059 A * | 2/1984 | Chang et al. ............ 436/512 |
| 4,861,581 A | 8/1989 | Epstein et al. | |
| 5,171,665 A | 12/1992 | Hellstrom et al. | |
| 5,484,596 A | 1/1996 | Hanna, Jr. et al. | |
| 5,693,763 A | 12/1997 | Codington et al. | |
| 5,750,102 A | 5/1998 | Eisenbach et al. | |
| 5,780,033 A | 7/1998 | Torchilin et al. | |
| 5,783,186 A | 7/1998 | Arakawa et al. | |
| 5,849,876 A | 12/1998 | Linsley et al. | |
| 5,869,045 A | 2/1999 | Hellstrom et al. | |
| 5,869,268 A | 2/1999 | Kudo et al. | |
| 7,189,825 B2 * | 3/2007 | Young et al. ............ 530/388.1 |
| 2003/0138425 A1 * | 7/2003 | Mather .................... 424/146.1 |

OTHER PUBLICATIONS

T. Nishihara et al, "Antibody-dependent cytotoxicity mediated by chimeric monoclonal antibody Nd2 and experimental immunotherapy for pancreatic cancer", Jpn. J. Cancer Res., 91:817-824 (Aug. 2000).

S. Green et al, "Disruption of cell-cell adhesion enhances antibody-dependent cellular cytotoxicity: implications for antibody-based therapeutics of cancer", Cancer Research, 62:6891-6900 (Dec. 2000).

D. Buchsbaum et al, "Antitumor efficacy of TRA-8 anti-DR5 monoclonal antibody alone or in combination with chemotherapy and/or radiation therapy in a human breast cancer model", Clinical Cancer Research, 9:3731-3741 (Sep. 2003).

* cited by examiner

*Primary Examiner*—Larry R. Helms
*Assistant Examiner*—Anne M. Gussow
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

17 Claims, 6 Drawing Sheets

FIGURE 2

| Table 1 | Isotype ELISA Fold | | Percentage Cytotoxicity | | | | | | Binding | | |
|---|---|---|---|---|---|---|---|---|---|---|---|
| | | | PC-3 | | LnCap | | CCD-27sk | | | | |
| | IgG | IgM | Average | CV | Average | CV | Average | CV | PC-3 Fold | LnCap Fold | CCD-27sk Fold |
| AR40A603.13 | 14.7 | 1.6 | 13 | 12 | 13 | 2 | -41 | 6 | 6.5 | 20.8 | 4.8 |
| Cycloheximide (Controls) | | | 58 | 6 | 31 | 49 | 37 | 12 | | | |
| NaN$_3$ (Controls) | | | 53 | 6 | 79 | 5 | 16 | 23 | | | |

FIGURE 3

| Table 2 | | COLON | | PANCREAS | BREAST | | PROSTATE | | | OVARY | NORMAL |
|---|---|---|---|---|---|---|---|---|---|---|---|
| Cell Line | DLD-1 | Lovo | SW1116 | BxPC-3 | MB-231 | MCF-7 | PC-3 | LnCap | DU-145 | OVCAR-3 | CCD-27sk | H9888 Lu |
| AR40A603.13 | | | ++ | + | | ++++ | | + | | + | + | |
| Negative Controls — 107.3 (IgG1) | | ++++ | | | + | | ++++ | | + | | +/- | |
| Negative Controls — IgG buffer (3%) | | | | | | | | | | | | |
| Positive Controls — anti-EGFR | +++ | ++++ | | | +/- | | ++++ | + | ++ | +++ | ++++ | |
| Positive Controls — CHX | +++ | ++++ | ++ | ++++ | ++++ | +++ | ++++ | +++ | +++ | ++++ | ++++ | ++++ |

FIGURE 4

| Table 3 | COLON | | | PANCREAS | BREAST | | PROSTATE | | | OVARY | NORMAL | |
|---|---|---|---|---|---|---|---|---|---|---|---|---|
| Cell Line | DLD-1 | Lovo | SW1116 | BxPC-3 | MB-231 | MCF-7 | PC-3 | LnCap | DU-145 | OVCAR-3 | CCD-27sk | Hs888 Lu |
| AR40A603.13 | +++ | ++ | +++ | ++++ | +++ | +++ | ND | ND | +++ | +++ | + | ++ |
| anti-EGFR (Positive Control) | ++ | + | ++ | ++ | +++ | | ++ | ND | ++ | ++ | + | ++ |

CANCEROUS DISEASE MODIFYING ANTIBODIES

REFERENCE TO RELATED APPLICATIONS

This application claims benefit of the filing date of Provisional Application 60/548,531, filed on Feb. 26, 2004, the contents of which is herein incorporated by reference.

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays, which utilize the CDMAB of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy, which lends itself to customization, is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells.

Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anticancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remissions or responses. Furthermore, there was a lack of reproducibility and no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least 4 clinical trials for human breast cancer which produced only 1 responder from at least 47 patients using antibodies against specific antigens or based on tissue selectivity. It was not until 1998 that there was a successful clinical trial using a humanized anti-Her2 antibody in combination with Cisplatin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung cancer, brain cancers, ovarian cancers, pancreatic cancer, prostate cancer, and stomach cancer. There has been some limited success in the use of anti-GD3 monoclonal antibodies for melanoma. Thus, it can be seen that despite successful small animal studies that are a prerequisite for human clinical trials, the antibodies that have been tested thus far have been, for the most part, ineffective.

Prior Patents:

U.S. Pat. No. 5,750,102 discloses a process wherein cells from a patient's tumor are transfected with MHC genes, which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies, which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas is not dependent upon the epithelial tissue of origin.

U.S. Pat. No. 5,783,186 is drawn to anti-Her2 antibodies, which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated in addition the patent discloses natural and monoclonal anti-nuclear autoantibody from an aged mammal, and a hybridoma cell line producing a monoclonal anti-nuclear autoantibody.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease.

This application utilizes, in part, the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

Furthermore, it is within the purview of this invention to conjugate standard chemotherapeutic modalities, e.g. radionuclides, with the CDMAB of the instant invention, thereby focusing the use of said chemotherapeutics.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibodies conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cellular cytotoxicity (ADCC) or complement-dependent cytotoxicity (CDC). For example murine IgM and IgG2a antibodies can activate human complement by binding the C-1 component of the complement system thereby activating the classical pathway of complement activation, which can lead to tumor lysis. For human antibodies the most effective complement-activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody-mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody-mediated cancer cell killing which are more widely accepted. The first is the use of antibodies as a vaccine to induce the body to produce an immune response against the putative cancer antigen that resides on the tumor cell. The second is the use of antibodies to target growth receptors and interfere with their function or to down regulate that receptor so that its function is effectively lost.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematology 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

Accordingly, it is an objective of the invention to utilize a method for producing CDMAB from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through antibody dependent cellular toxicity.

It is yet an additional objective of the instant invention to produce CDMAB whose cytotoxicity is mediated through complement dependent cellular toxicity.

It is still a further objective of the instant invention to produce CDMAB whose cytotoxicity is a function of their ability to catalyze hydrolysis of cellular chemical bonds.

A still further objective of the instant invention is to produce CDMAB, which are useful in a binding assay for diagnosis, prognosis, and monitoring of cancer.

Other objects and advantages of this invention will become apparent from the following description wherein, by way of illustration and example, certain embodiments of this invention are set forth.

BRIEF DESCRIPTION OF THE FIGURES

FIG. 2 compares the percentage cytotoxicity of the hybridoma supernatants against cell lines PC-3, LnCap and CCD-27sk versus binding levels;

FIG. 3 is a comparison of cytotoxicity of AR40A603.13 versus positive and negative controls;

FIG. 4 represents binding of AR40A603.13 versus anti-EGFR control and tabulated the mean fluorescence intensity fold increase above isotype control. Results are presented qualitatively as: between 1.5 to 5 (+); 5 to 25 (++); 25 to 50 (+++); and above 50 (++++);

DETAILED DESCRIPTION OF THE INVENTION

EXAMPLE 1

Hybridoma Production—Hybridoma Cell Line AR40A603.13

Figure 1:
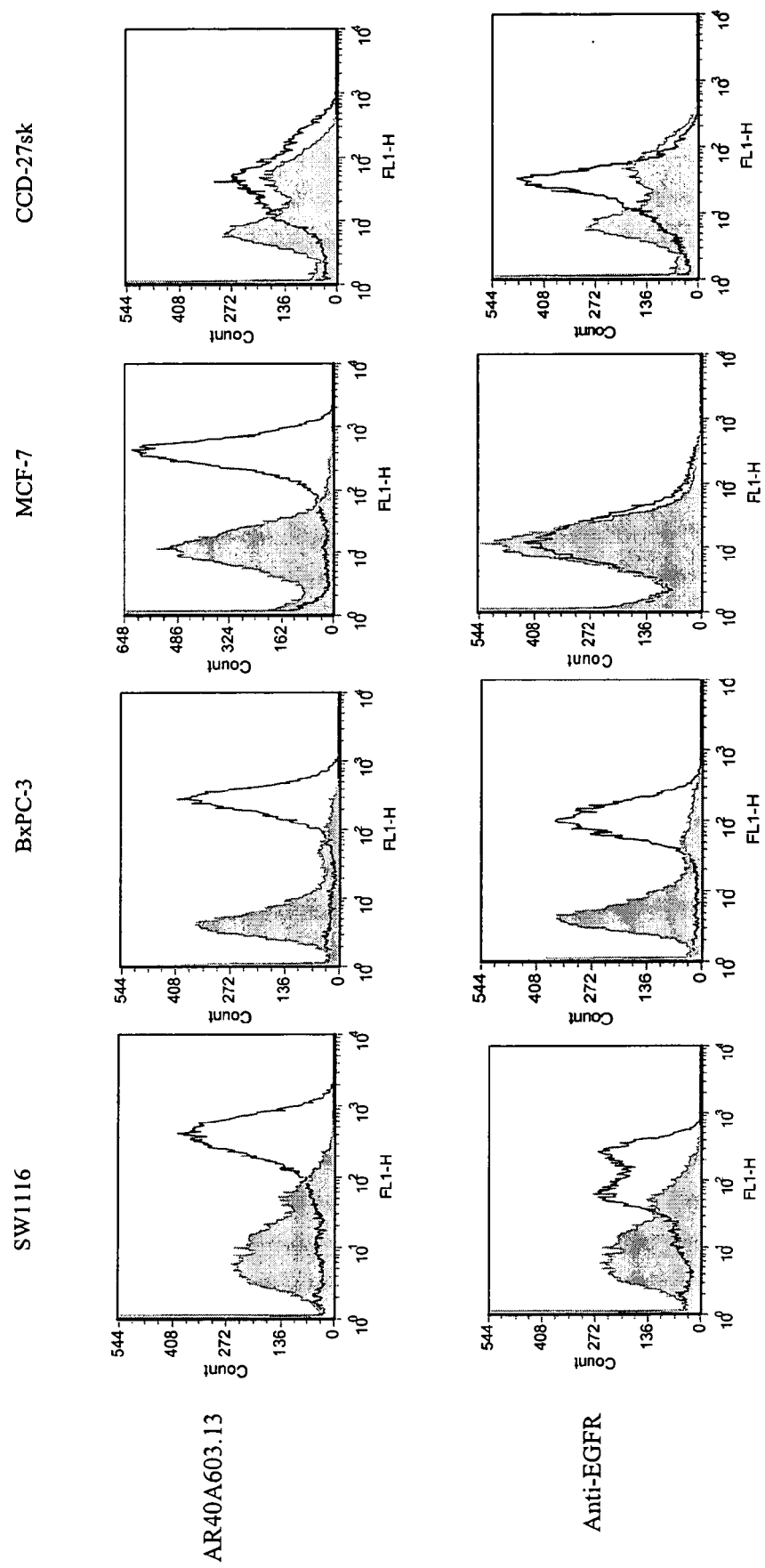
FIG. 1 includes representative FACS histograms of AR40A603.13 and anti-EGFR antibodies directed against several cancer and non-cancer cell lines.
Figure 5:
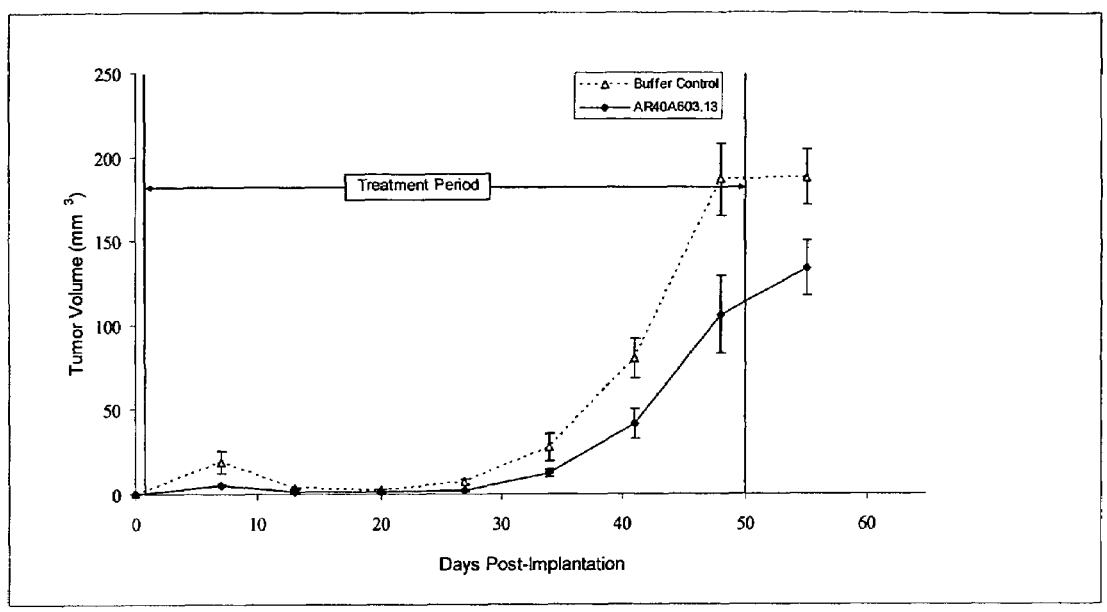
FIG. 5 demonstrates the effect of AR40A603.13 on tumor growth in a SW1116 colon cancer model. The vertical lines indicate the period during which the antibody was administered. Data points represent the mean +/- SEM.

The hybridoma cell line AR40A603.13 was deposited, in accordance with the Budapest Treaty, with the International Depository Authority of Canada (IDAC), Bureau of Microbiology, Health Canada, 1015 Arlington Street, Winnipeg, Manitoba, Canada, R3E 3R2, on Jan. 28, 2004, under Accession Number 280104-04. In accordance with 37 CFR 1.808, the depositors assure that all restrictions imposed on the availability to the public of the deposited materials will be irrevocably removed upon the granting of a patent.

To produce the hybridoma that produces the anti-cancer antibody AR40A603.13, a single cell suspension of frozen human prostate tumor tissue (Genomics Collaborative, Cambridge, Mass.) was prepared in PBS. IMMUNEASY™ (Qiagen, Venlo, Netherlands) adjuvant was prepared for use by gentle mixing. Five to seven week old BALB/c mice were immunized by injecting subcutaneously, 2 million cells in 50 microliters of the antigen-adjuvant. Recently prepared antigen-adjuvant was used to boost the immunized mice intraperitoneally, 2 and 5 weeks after the initial immunization, with 2 million cells in 50 microliters. A spleen was used for fusion three days after the last immunization. The hybridomas were prepared by fusing the isolated splenocytes with NSO-1 myeloma partners. The supernatants from the fusions were tested for subcloning of the hybridomas.

To determine whether the antibodies secreted by the hybridoma cells are of the IgG or IgM isotype, an ELISA assay was employed. 100 microliters/well of goat anti-mouse IgG+IgM (H+L) at a concentration of 2.4 micrograms/mL in coating buffer (0.1M carbonate/bicarbonate buffer, pH 9.2-9.6) at 4° C. was added to the ELISA plates overnight. The plates were washed thrice in washing buffer (PBS+0.05% Tween). 100 microliters/well blocking buffer (5% milk in wash buffer) was added to the plate for 1 hr. at room temperature and then washed thrice in washing buffer. 100 microliters/well of hybridoma supernatant was added and the plate incubated for 1 hr. at room temperature. The plates were washed thrice with washing buffer and 1/100,000 dilution of either goat anti-mouse IgG or IgM horseradish peroxidase conjugate (diluted in PBS containing 5% milk), 100 microliters/well, was added. After incubating the plate for 1 hr. at room temperature the plate was washed thrice with washing buffer. 100 microliters/well of TMB solution was incubated for 1-3 minutes at room temperature. The color reaction was terminated by adding 100 microliters/well 2M $H_2SO_4$ and the plate was read at 450 nm with a Perkin-Elmer HTS7000 plate reader. As indicated in FIG. 2, the AR40A603.13 hybridoma secreted primarily antibodies of the IgG isotype.

After one round of limiting dilution hybridoma supernatants were tested for antibodies that bound to target cells in a cell ELISA assay. Two human prostate cancer cell lines and 1 human normal skin cell line were tested: PC-3, LnCap and CCD-27sk respectively. The plated cells were fixed prior to use. The plates were washed thrice with PBS containing $MgCl_2$ and $CaCl_2$ at room temperature. 100 microliters of 2% paraformaldehyde diluted in PBS was added to each well for 10 minutes at room temperature and then discarded. The plates were again washed with PBS containing $MgCl_2$ and $CaCl_2$ three times at room temperature. Blocking was done with 100 microliters/well of 5% milk in wash buffer (PBS+0.05% Tween) for 1 hr at room temperature. The plates were washed thrice with wash buffer and the hybridoma supernatant was added at 100 microliters/well for 1 hr at room temperature. The plates were washed 3 times with wash buffer and 100 microliters/well of 1/25,000 dilution of goat anti-mouse IgG or IgM antibody conjugated to horseradish peroxidase (diluted in PBS containing 5% milk) was added. After 1 hr incubation at room temperature the plates were washed 3 times with wash buffer and 100 microliter/well of TMB substrate was incubated for 1-3 minutes at room temperature. The reaction was terminated with 100 microliters/well 2M $H_2SO_4$ and the plate read at 450 nm with a Perkin-Elmer HTS7000 plate reader. The results as tabulated in FIG. 2 were expressed as the number of folds above background compared to an in-house IgG isotype control that has previously been shown not to bind to the cell lines tested. The antibodies from the hybridoma AR40A603.13 showed substantial binding to the prostate cancer cell line LnCap, followed by another prostate cancer cell line PC-3. AR40A603.13 displayed the lowest level of binding to the normal skin cell line CCD-27sk.

In conjunction with testing for antibody binding the cytotoxic effect of the hybridoma supernatants were tested in the same cell lines: PC-3, LnCap and CCD-27sk. The Live/Dead cytotoxicity assay was obtained from Molecular Probes (Eu, OR). The assays were performed according to the manufacturer's instructions with the changes outlined below. Cells were plated before the assay at the predetermined appropriate density. After 2 days, 100 µl of supernatant from the hybridoma microtitre plates were transferred to the cell plates and incubated in a 5 percent $CO_2$ incubator for 5 days. The wells that served as the positive controls were aspirated until empty and 100 µl of sodium azide ($NaN_3$) or cycloheximide was added. After 5 days of treatment, the plates were then emptied by inverting and blotting dry. Room temperature DPBS (Dulbecco's phosphate buffered saline) containing $MgCl_2$ and $CaCl_2$ was dispensed into each well from a multichannel squeeze bottle, tapped 3 times, emptied by inversion and then blotted dry. 50 µl of the fluorescent calcein dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel. The results are tabulated in FIG. 2. The AR40A603.13 hybridoma produced specific cytotoxicity of 13 percent on both the PC-3 and LnCap cells, which was 24 and 22 percent of the cytotoxicity obtained in the PC-3 cells and likewise, 16 and 42 percent in the LnCap cells, with the positive controls sodium azide and cycloheximide respectively. Results from FIG. 2 demonstrated that the cytotoxic effects of AR40A603.13 were not proportional to the binding levels on the two cancer cell types. There was the same level of cytotoxicity produced in both the LnCap and PC-3 cells. However, there was at least a three-fold increase in binding of AR40A603.13 to LnCap versus PC-3 cells. As tabulated in FIG. 2, AR40A603.13 did not produce cytotoxicity in the CCD-27sk normal cell line despite substantial binding to these cells. The known non-specific cytotoxic agents cycloheximide and $NaN_3$ generally produced cytotoxicity as expected.

EXAMPLE 2

Antibody Production:

AR40A603.13 monoclonal antibody was produced by culturing the hybridoma in CL-1000 flasks (BD Biosciences, Oakville, ON) with collections and reseeding occurring twice/week. Standard antibody purification procedures with Protein G Sepharose 4 Fast Flow (Amersham Biosciences, Baie d'Urfé, QC) were followed. It is within the scope of this invention to utilize monoclonal antibodies that are humanized, chimerized or murine.

AR40A603.13 was compared to a number of both positive (anti-EGFR (C225, IgG1, kappa, 5 µg/mL, Cedarlane, Homby, ON), cycloheximide (CHX, 0.5 µM, Sigma, Oakville, ON), and $NaN_3$ (0.1%, Sigma, Oakville, ON)) and negative (107.3 (anti-TNP), IgG1, kappa, 20 µg/mL, BD Bioscience, Oakville, ON), and IgG Buffer (3%)) controls in a cytotoxicity assay (FIG. 3). Breast (MDA-MB-231 (MB- 231), NCI-MCF-7 (MCF-7)), colon (DLD-1, Lovo, SW1116), ovarian (OVCAR-3), pancreatic (BxPC-3), and prostate (PC-3, LnCap, DU-145) cancer, and non-cancer skin (CCD-27sk), and lung (Hs888.Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, 100 µl of purified antibody or controls were diluted into media, and then transferred to the cell plates and incubated in a 5 percent $CO_2$ incubator for 5 days. The plates were then emptied by inverting and blotted dry. Room temperature DPBS containing $MgCl_2$ and $CaCl_2$ was dispensed into each well from a multichannel squeeze bottle, tapped 3 times, emptied by inversion and then blotted dry. 50 µl of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel and the results were tabulated in FIG. 3. The data was represented as an average of four experiments tested in triplicate and is presented qualitatively in the following fashion: ¾ to 4/4 experiments with >15% cytotoxicity above background (++++), 2/4 experiments with >15% cytotoxicity above background (+++), at least 2/4 experiments with 10-15% cytotoxicity above background (++), at least 2/4 experiments with 8-10% cytotoxicity above background (+), 7% cytotoxicity above background (+/−). Unmarked cells in FIG. 3 represented inconsistent or effects less than the threshold cytotoxicity. The AR40A603.13 antibody produced cytotoxicity in the SW1116 colon cancer cell line, the MCF-7 breast cancer cell line, the OVCAR-3 ovarian cancer cell line, the LnCap prostate cancer cell line and the BxPC-3 pancreatic cancer cell line relative to both isotype and buffer negative controls. Importantly, AR40A603.13 did not produce significant cytotoxicity, above negative controls, against non-cancer cell lines such as CCD-27sk or Hs888.Lu, indicating that the antibody has specificity towards cancer cells. The chemical cytotoxic agents induced their expected non-specific cytotoxicity.

Binding of AR40A603.13 to the above-mentioned panel of cancer and normal cell lines was assessed by flow cytometry (FACS). Cells were prepared for FACS by initially washing the cell monolayer with DPBS (without $Ca^{++}$ and $Mg^{++}$). Cell dissociation buffer (INVITROGEN, Burlington, ON) was then used to dislodge the cells from their cell culture plates at 37° C. After centrifugation and collection, the cells were resuspended in DPBS containing $MgCl_2$, $CaCl_2$ and 2 percent fetal bovine serum at 4° C. (staining media) and counted, aliquoted to appropriate cell density, spun down to pellet the cells and resuspended in staining media at 4° C. in the presence of test antibodies (AR40A603.13) or control antibodies (isotype control, anti-EGFR) at 20 µg/mL on ice for 30 minutes. Prior to the addition of Alexa Fluor 488-conjugated secondary antibody the cells were washed once with staining media. The Alexa Fluor 488-conjugated antibody in staining media was then added for 30 minutes. The cells were then washed for the final time and resuspended in fixing media (staining media containing 1.5% paraformaldehyde). Flow cytometric acquisition of the cells was assessed by running samples on a FACScan using the CellQuest software (BD Biosciences, Oakville, ON). The forward (FSC) and side scatter (SSC) of the cells were set by adjusting the voltage and amplitude gains on the FSC and SSC detectors. The detectors for the fluorescence (FITC) channel was adjusted by running cells stained only with Alexa Fluor 488-conjugated secondary antibody such that cells had a uniform peak with a median fluorescent intensity of approximately 1-5 units. For each sample, approximately 10,000 stained fixed cells were acquired for analysis and the results are presented in FIG. 4.

FIG. 4 tabulated the mean fluorescence intensity fold increase above isotype control and is presented qualitatively as: between 1.5 to 5 (+); 5 to 25 (++); 25 to 50 (+++); and above 50 (++++). Representative histograms of AR40A603.13 antibodies were compiled for FIG. 1. AR40A603.13 showed binding to all cell lines tested. These data have demonstrated that AR40A603.13 exhibited functional specificity in that although there was clear binding to all cancer types tested, there was only associated cytotoxicity with SW1116, MCF-7, OVCAR-3, LnCap and BxPC-3 cancer cells types. By contrast, the anti-EGFR antibody displayed a higher correlation between binding and cytotoxicity with one such example being the non-cancer epidermis derived cell line, CCD-27sk. AR40A603.13 was also effective in several cancer cell lines that were not affected by anti-EGFR, including SW1116, BxPC-3 and MCF-7.

EXAMPLE 3

In Vivo SW1116 Tumor Experiments

With reference to FIGS. 5 and 6, 4 to 8 week old female SCID mice were implanted with 5 million human colon cancer cells (SW1116) in 100 microlitres saline injected subcutaneously in the scruff of the neck. The mice were randomly divided into 2 treatment groups of 5. On the day after implantation, 20 mg/kg of AR40A603.13 test antibody or buffer control was administered intraperitoneally at a volume of 300 microliters after dilution from the stock concentration with a diluent that contained 2.7 mM KCl, 1 mM $KH_2PO_4$, 137 mM NaCl and 20 mM $Na_2HPO_4$. The antibodies were then administered once per week for a period of 7 weeks in the same fashion. Tumor growth was measured about every seventh day with calipers for up to 8 weeks or until individual animals reached the Canadian Council for Animal Care (CCAC) end-points. Body weights of the animals were recorded for the duration of the study. At the end of the study all animals were euthanised according to CCAC guidelines.

AR40A603.13 prevented tumor growth and reduced tumor burden in a preventative in vivo model of human colon cancer. On day 55 post-implantation, 5 days after the last treatment dose, the mean tumor volume in the AR40A603.13 treated group was 71 percent of the tumor volume in the buffer control-treated group (p=0.0493, t-test, FIG. 5).

Figure 6:
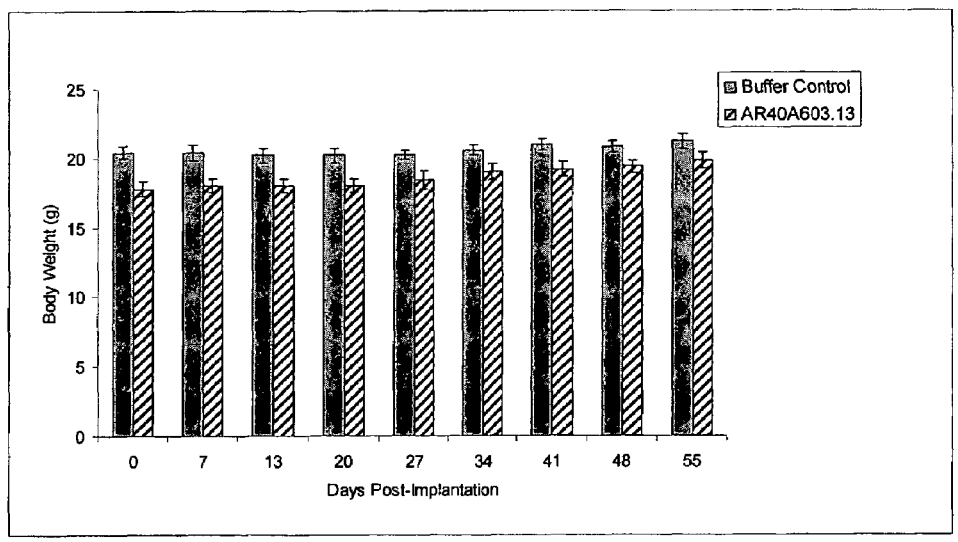
FIG. 6 demonstrates the effect of AR40A603.13 on body weight in a SW1116 colon cancer model. Data points represent the mean +/- SEM.
Figure 7:
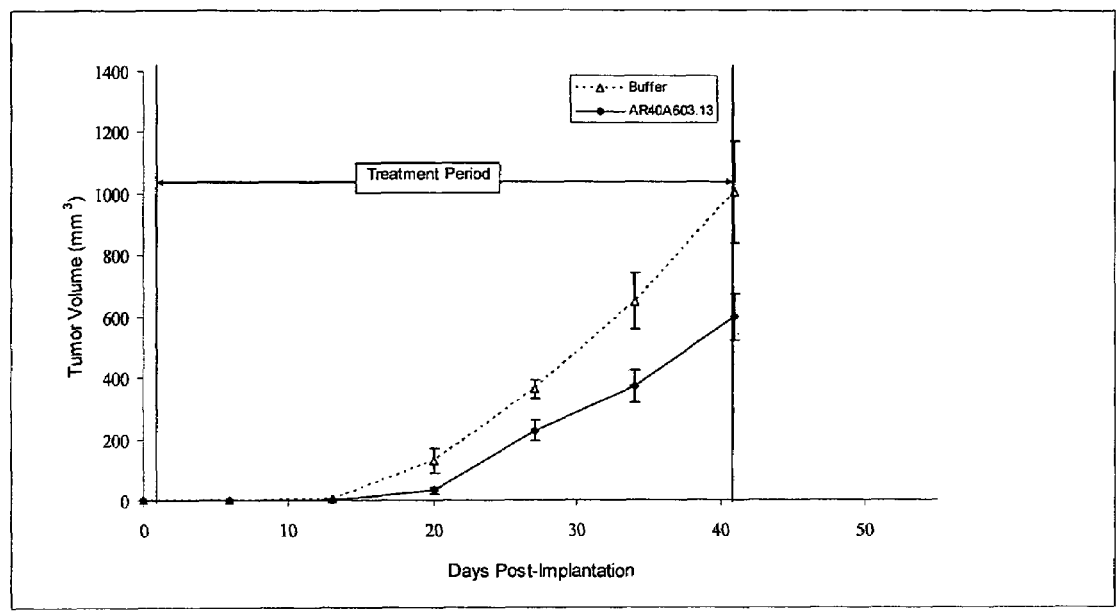
FIG. 7 demonstrates the effect of AR40A603.13 on tumor growth in a PC-3 colon cancer model. The vertical lines indicate the period during which the antibody was administered. Data points represent the mean +/- SEM.

There were no clinical signs of toxicity throughout the study. Body weight measured at weekly intervals was a surrogate for well-being and failure to thrive. As seen in FIG. 6, there was no significant difference in body weight between the groups at the end of the treatment period (p=0.1152, t-test). Within groups, the body weight of the buffer treated control animals did not vary significantly between the start and end of the study period (p=0.2825, t-test), while the body weight of the AR40A603.13 treated group showed a slight significant increase from a mean of 17.80 g to 19.80 g (p=0.0345, t-test).

Therefore AR40A603.13 was well-tolerated and decreased the tumor burden in a colon cancer xenograft model.

EXAMPLE 4

In Vivo PC-3 Tumor Experiments

With reference to FIGS. 7 and 8, 4 to 8 week old male SCID mice were implanted with 1 million human prostate cancer cells (PC-3) in 100 microlitres saline injected subcutaneously in the scruff of the neck. The mice were randomly divided into 2 treatment groups of 5. On the day after implantation, 20 mg/kg of AR40A603.13 test antibody or buffer control was administered intraperitoneally at a volume of 300 microliters after dilution from the stock concentration with a diluent that contained 2.7 mM KCl, 1 mM $KH_2PO_4$, 137 mM NaCl and 20 mM $Na_2HPO_4$. The antibodies were then administered once per week for the duration of the study in the same fashion. Tumor growth was measured about every seventh day with calipers. The study was completed after 6 injections (41 days), as the animals reached the Canadian Council for Animal Care (CCAC) end-points due to large ulcerated lesions. Body weights of the animals were recorded for the duration of the study. At the end of the study all animals were euthanised according to CCAC guidelines.

AR40A603.13 prevented tumor growth and reduced tumor burden in a preventative in vivo model of human prostate cancer. On day 41 post-implantation, 5 days after the last treatment dose, the mean tumor volume in the AR40A603.13 treated group was 60 percent of the tumor volume in the buffer control-treated group (p=0.055, t-test, FIG. 7).

Figure 8:
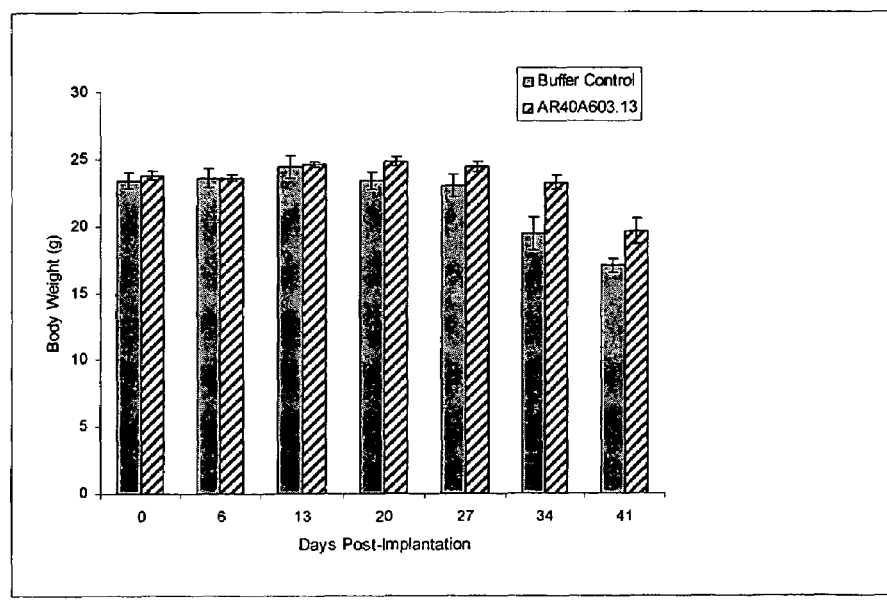
FIG. 8. demonstrates the effect of AR40A603.13 on body weight in a PC-3 prostate cancer model. Data points represent the mean +/- SEM.

In a PC-3 prostate cancer xenograft model, body weight can be used as a surrogate indicator of disease progression (Wang et al. Int J Cancer, 2003). As seen in FIG. 8, by the end of the study, day 41, control animals exhibited a 27% decrease in body weight from the onset of the study. By contrast, the group treated with AR40A603.13 had a significantly higher body weight than the control group (p=0.0465, t-test). Overall, the AR40A603.13-treated group lost 36% less weight than the buffer control group. Therefore AR40A603.13 was well-tolerated and decreased the tumor burden and cachexia in a prostate cancer xenograft model.

REFERENCE

Wang Z, Corey E, Hass G M, et al. Expression of the human cachexia-associated protein (HCAP) in prostate cancer and in a prostate cancer animal model of cachexia. Int J Cancer. 2003; 105(1):123-9.

What is claimed is:

1. The isolated monoclonal antibody produced by the hybridoma deposited with the IDAC as Accession Number 280104-04.

2. A humanized antibody of the isolated monoclonal antibody of claim 1.

3. A chimeric antibody of the isolated monoclonal antibody of claim 1.

4. The isolated hybridoma deposited with the IDAC as Accession Number 280104-04.

5. A method for initiating antibody induced cellular cytotoxicity of cancerous cells in a tissue sample selected from a human tumor comprising:

providing a tissue sample from said human tumor;

providing an isolated monoclonal antibody encoded by the hybridoma deposited with the IDAC as Accession Number 280104-04 or a cellular cytotoxicity inducing antigen binding fragment thereof; and contacting said isolated monoclonal antibody or cellular cyrotoxicity inducing antigen binding fragment thereof with said tissue sample.

6. The method of claim 5 wherein the human tumor tissue sample is obtained from a rumor originating in a tissue selected from the group consisting of colon, ovarian, prostate, pancreatic and breast tissue.

7. Antigen binding fragments of the isolated monoclonal antibody of claim 1.

8. Antigen binding fragments of the humanized antibody of claim 2.

9. Antigen binding fragments of the chimeric antibody of claim 3.

10. The isolated antibody or antigen binding fragments of any one of claims 1,2,3,7,8 or 9 conjugated with a member selected from the group consisting of cytotoxic moieties, enzymes, radioactive compounds, and hematogenous cells.

11. A method of treating a human tumor susceptible to antibody induced cellular cytotoxicity in a mammal, wherein said human tumor expresses an antigen which specifically binds to the monoclonal antibody which has the cellular cytotoxicity inducing characteristics of the monoclonal antibody encoded by a hybridoma deposited with the IDAC as Accession Number 280104-04 or a cellular cytotoxicity inducing antigen binding fragment thereof, comprising administering to said mammal said monoclonal antibody or said antigen binding fragment thereof in an amount effective to induce cellular cytotoxicity and thereby reduce said mammal's tumor burden.

12. The method of claim 11 wherein said monoclonal antibody is conjugated to a cytotoxic moiety.

13. The method of claim 12 wherein said cytotoxic moiety is a radioactive isotope.

14. The method of claim 11 wherein said monoclonal antibody activates complement.

15. The method of claim 11 wherein said monoclonal antibody mediates antibody dependent cellular cytotoxicity.

16. The method of claim 11 wherein said monoclonal antibody is humanized.

17. The method of claim 11 wherein said monoclonal antibody is chimeric.

* * * * *